United States Patent
Nakashima et al.

(10) Patent No.: US 7,138,515 B2
(45) Date of Patent: Nov. 21, 2006

(54) TRANSLATIONAL ACTIVITY-PROMOTING HIGHER-ORDER STRUCTURE

(75) Inventors: Nobuhiko Nakashima, Tsukuba (JP); Yasushi Kanamori, Tsukuba (JP)

(73) Assignee: National Institute of Agrobiological Sciences, Ibaraki (JP)

( * ) Notice: Subject to any disclaimer, the term of this patent is extended or adjusted under 35 U.S.C. 154(b) by 538 days.

(21) Appl. No.: 10/088,750

(22) PCT Filed: Jan. 31, 2001

(86) PCT No.: PCT/JP01/00641

§ 371 (c)(1),
(2), (4) Date: Mar. 20, 2002

(87) PCT Pub. No.: WO02/061080

PCT Pub. Date: Aug. 8, 2002

(65) Prior Publication Data

US 2004/0166486 A1    Aug. 26, 2004

(30) Foreign Application Priority Data

Jan. 25, 2001 (JP) ............................ 2001-016746

(51) Int. Cl.
*C07H 21/02* (2006.01)
*C12Q 1/70* (2006.01)
(52) U.S. Cl. ........................ 536/23.72; 435/5; 435/325; 435/320.1; 435/456
(58) Field of Classification Search ............. 536/23.72; 435/5, 325, 320.1, 456
See application file for complete search history.

(56) References Cited

OTHER PUBLICATIONS

Sasaki et al., J. Virology, 73, 1219-1226, (Feb. 1999).*
Sasaki et al., PNAS 97, No. 4, 1512-1515 (Feb. 2000).*

* cited by examiner

*Primary Examiner*—Chih-Min Kam
(74) *Attorney, Agent, or Firm*—Kilyk & Bowersox, P.L.L.C.

(57) ABSTRACT

The present invention was conceived from the findings; that a specific higher-order structure can be formed in CrP-like viruses; that linkage of a gene reading frame downstream in the higher-order structure permits initiating the translation of a protein from various amino acids; and that a change in the combination of base pairs involved in the formation of the higher-order structure immediately upstream in the translation initiation site permits initiating the synthesis of any protein from any codon.

10 Claims, 9 Drawing Sheets

SEQUENCE LISTING

<160> NUMBER OF SEQ ID NOS: 12

<210> SEQ ID NO 1
<211> LENGTH: 200
<212> TYPE: RNA
<213> ORGANISM: Plautia Stali Intestine Virus

<400> SEQUENCE: 1
gacuauguga ucuuauuaaa auuagguuaa auuucgaggu uaaaaauagu uuuaauauug     60
cuauagucuu agaggucuug uauauuuaua cuuaccacac aagauggacc ggagcagccc    120
uccaauaucu aguguacccu cgugcucgcu caaacauuaa guggguugu gcgaaaagaa    180 ucucacuuca agaaaaagaa                                                200

<210> SEQ ID NO 2
<211> LENGTH: 199
<212> TYPE: RNA
<213> ORGANISM: Himetobi P Virus

<400> SEQUENCE: 2
gaaaaugugu gaucugauua gaaguaagaa auuccuagu uauaauauuu uuaauacugc      60
uacauuuuua agacccuuag uuauuuagcu uuaccgccca ggaugggug cagcguuccu    120 gcaauaucca gggcaccuag gugcagccuu guaguuuuag uggacuuuag gcuaaagaau   180
uucacuagca aauaauaau                                                199

<210> SEQ ID NO 3
<211> LENGTH: 201
<212> TYPE: RNA
<213> ORGANISM: Drosophila C Virus

<400> SEQUENCE: 3
guuaagaugu gaucuugcuu ccuuauacaa uuuugagagg uuaauaagaa ggaaguagug     60
cuaucuuaau aauuagguua acuauuuagu uuuacuguuc aggaugccua uuggcagccc   120
cauaauaucc aggacacccu cucugcuucu uauaugauua gguugcauu uagaauaaga   180 aaauaaccug cuaacuuuca a                                              201

<210> SEQ ID NO 4
<211> LENGTH: 200
<212> TYPE: RNA
<213> ORGANISM: Cricket Paralysis Virus

<400> SEQUENCE: 4
caaaaaugug aucuugcuug uaauacaau uuugagaggu uaauaaauua caaguagugc      60 uauuuugua uuagguuag cuauuuagcu uuacguucca ggaugccuag uggcagcccc    120
acaauaucca ggaagcccuc ucugcgguuu uucagauuag guagucgaaa aaccuaagaa   180
auuuaccugc uacauuucaa                                                200

<210> SEQ ID NO 5
<211> LENGTH: 198
<212> TYPE: RNA
<213> ORGANISM: Triatoma Virus

<400> SEQUENCE: 5
uugacuaugu gaucuugcuu ucguaauaaa aucuguacau aaaagucgaa aguauugcua    60
uaguuaaggu ugcgcuugcc uauuuaggca uacuucag gauggcgcgu ugcaguccaa    120

```
caagauccag ggacuguaca gaauuuuccu auaccucgag ucggguuugg aaucuaaggu      180
ugacucgcug uaaauaau                                                    198

<210> SEQ ID NO 6
<211> LENGTH: 202
<212> TYPE: RNA
<213> ORGANISM: Black Queen-Cell Virus

<400> SEQUENCE: 6
ccaacaaugu gaucuugcuu gcggaggcaa aauuugcaca guauaaaauc ugcaaguagu       60 gcuauguug gaaucaccgu accuauuuag guuuacgcuc caagaucggu ggauagcagc       120 ccaucaaua ucuaggagaa cugugcuaug uuuagaagau uagguagucu cuaaacagaa      180
caauuuaccu gcugaacaaa uu                                               202

<210> SEQ ID NO 7
<211> LENGTH: 187
<212> TYPE: RNA
<213> ORGANISM: Rhopalosiphum Padi Virus

<400> SEQUENCE: 7
aguguugugu gaucuugcgc gauaaaugcu gacgugaaaa cguugcguau ugcuacaaca       60
cuugguuagc uauuuagcuu uacuaaucaa gacgccgucg ugcagcccac aaaagucuag      120
auacgucaca ggagagcaua cgcuaggucg cguugacuau ccuuauauau gaccugcaaa      180
uauaaac                                                                187

<210> SEQ ID NO 8
<211> LENGTH: 29
<212> TYPE: DNA
<213> ORGANISM: Artificial
<220> FEATURE:
<223> OTHER INFORMATION: The sequence was synthesized for use as a
      forward primer.

<400> SEQUENCE: 8
ggttaaattt caggtaaaaa attgctata                                         29

<210> SEQ ID NO 9
<211> LENGTH: 35
<212> TYPE: DNA
<213> ORGANISM: Artificial
<220> FEATURE:
<223> OTHER INFORMATION: The sequence was synthesized for use as a
      reverse primer.

<400> SEQUENCE: 9
cctcgaaatt taaccagatc acatagtcag ctttc                                  35

<210> SEQ ID NO 10
<211> LENGTH: 281
<212> TYPE: RNA
<213> ORGANISM: Unknown
<220> FEATURE:
<223> OTHER INFORMATION: The sequence is used only to illustrate
      secondary structures predicted by a computer program, MFOLD, as
      shown in Fig. 3.

<400> SEQUENCE: 10
cggugucgaa guagaauuuc uaucucgaca cgcggccuuc caagcaguua gggaaaccga       60
cuucuuugaa gaagaaagcu gacuauguga ucuuauuaaa auuggauuaa auuucgaggu      120
```

```
-continued uaauaaaagu uuuaauauug cuauagucuu agaggucuug uauauuuaua cuuaccacac      180
aagauggacc ggagcagccc uccaauaucu aguguacccu cgugcucgcu caaacauuaa      240
gugguguugu gcgaaaagaa ucucacuuca agaaaaagaa u                         281

<210> SEQ ID NO 11
<211> LENGTH: 16
<212> TYPE: RNA
<213> ORGANISM: Unknown
<220> FEATURE:
<223> OTHER INFORMATION: The sequence is used only to illustrate aspects
      of higher order structures on protein synthesis in Fig. 8A.

<400> SEQUENCE: 11
aacauuaagu gguguu                                                      16

<210> SEQ ID NO 12
<211> LENGTH: 16
<212> TYPE: RNA
<213> ORGANISM: Unknown
<220> FEATURE:
<223> OTHER INFORMATION: The sequence is used only to illustrate aspects
      of higher order structures on protein synthesis in Fig. 8A.

<400> SEQUENCE: 12 aacaugggu gguguu                                                       16
```

TRANSLATIONAL ACTIVITY-PROMOTING HIGHER-ORDER STRUCTURE

This application claims the benefit of earlier filed International Application No. PCT/JP01/00641 filed Jan. 31, 2001.

TECHNICAL FIELD

The present invention relates to a novel RNA higher-order structure having a function for promoting a translation activity. More particularly, the invention relates to base sequences making up a novel RNA higher-order structure or homologous structure thereof at an intergenic region-internal ribosome entry site (IGR-IRES) formed upstream of a coat protein coding region of cricket paralysis-like (CrP-like) viruses, and to a method for synthesizing a heterologous protein or a heterologous polypeptide using the base sequences.

BACKGROUND ART

AUG translation initiation codon coding methionine is needed on translating a messenger RNA (mRNA) by use of a ribosome to synthesize a protein. The reason is that a special tRNA molecule dedicated to translation initiation, in the form of translation initiation methionine tRNA serving to define the initiation codon, is indispensable for initiation of translation. Therefore, in the protein synthesis system utilizing the conventional recombination DNA technique, the amino terminus of a protein, polypeptide and the like, which is produced via ribosome, always leads to methionine. Accordingly, the synthesis of the protein initiating from an arbitrary amino acid had been impossible. Recently, however, a method was published that permits synthesizing a protein having an amino acid other than methionine at the amino terminus (Toku Hyo 2000-517186). This method utilizes a DNA coding a mutant initiator tRNA containing an anticodon corresponding to an amino acid other than methionine.

On the other hand, in the translation initiation via the intergenic region-internal ribosome entry site (IGR-IRES) of an insect virus, the translation initiation point is determined by forming higher-order structure of IGR-IRES per se, i.e., the translation is initiated from glutamine (Ref. 2) or alanine (Refs. 3, 4, 5, and 7) without depending on the AUG translation initiation codon. About 40 bases at 3' end of IGR-IRES had been reported (Ref 2), while the overall structure of IGR-IRES was not known. Previous reports (Refs. 1 and 6) had published a result showing that a partial sequence of the coding region of a coat protein gene of each virus locating downstream of IRES is also involved in the translation initiation, so that the translation initiation from the amino acid other than methionine, alanine, and glutamine had been thought to be impossible.

DESCRIPTION OF THE INVENTION

The inventors found that 1) a specific higher-order structure is formed in all CrP-like viruses, 2) linking a reading frame of a gene downstream of the higher-order structure permits the translation initiation of a protein from one of various amino acids, and 3) changing the combination of the base pair involved in the formation of the higher-order structure immediately upstream of the translation initiation site permits the initiation of the synthesis of an arbitrary protein from an arbitrary codon, and have completed the present invention.

An aspect of the present invention provides an RNA higher-order structure with promoting a translation activity and including a base sequence selected from the group consisting of:
1) a base sequence expressed by sequences designated in Sequence Nos. 1 to 7 of the sequence list;
2) a base sequence containing the base sequence of 1);
3) a base sequence that has at least about 50% of homology in sequence to the base sequence of 1) and that has a translation activity-promoting ability;
4) a complementary strand of the base sequences of 1) to 3);
5) a base sequence hybridizing with the base sequences of 1) to 4) under stringent conditions; and
6) a base sequence that has been mutated by deletion, substitution, addition, or insertion of one or more base(s) in the base sequences of 1) to 5) and that has a property for promoting translation activity.

Another aspect of the present invention provides an RNA higher-order structure having at least PK (pseudoknot) I, II, and III structures in the above higher-order structure.

Yet another aspect of the present invention provides a recombinant vector that contains a polynucleotide consisting of any one of base sequences having the above higher-order structure.

Still another aspect of the present invention provides a transformant that has been transformed with the above recombinant vector.

Yet still another aspect of the present invention provides a method for synthesizing a heterologous protein or a heterologous polypeptide utilizing a polynucleotide that consists of any one of the base sequences having a higher-order structure.

Still yet another aspect of the present invention provides a method for synthesizing a heterologous protein or a heterologous polypeptide utilizing the vector or the transformant.

Further aspect of the present invention provides a method for synthesizing a heterologous protein or heterologous polypeptide, wherein the synthesis is carried out using the vector in a cell-free protein synthesis system.

Yet further aspect of the present invention provides the method for synthesizing a heterologous protein or heterologous polypeptide, wherein the synthesis is carried out using the vector in a cell-free protein synthesis system that uses a wheat germ extract.

Still further aspect of the present invention provides the method for synthesizing a heterologous protein or polypeptide without using the AUG translation initiation codon.

Yet still further aspect of the present invention provides a method for initiating the synthesis of any heterologous protein or heterologous polypeptide from any codon, the method comprising the steps of changing the combination of base pairs that make up a PK (pseudoknot) in the RNA higher-order structure; and utilizing a base sequence having the changed higher-order structure.

Still yet further aspect of the present invention provides a method for initiating the synthesis of any heterologous protein or heterologous polypeptide from any codon, the method comprises the steps of changing one or more combination(s) of base pairs immediately upstream of the translation initiation site among combinations of base pairs that make up PK (pseudoknot) I in the RNA higher-order structure, and utilizing a base sequence having the changed higher-order structure.

DESCRIPTION OF DRAWINGS

Figure 1:
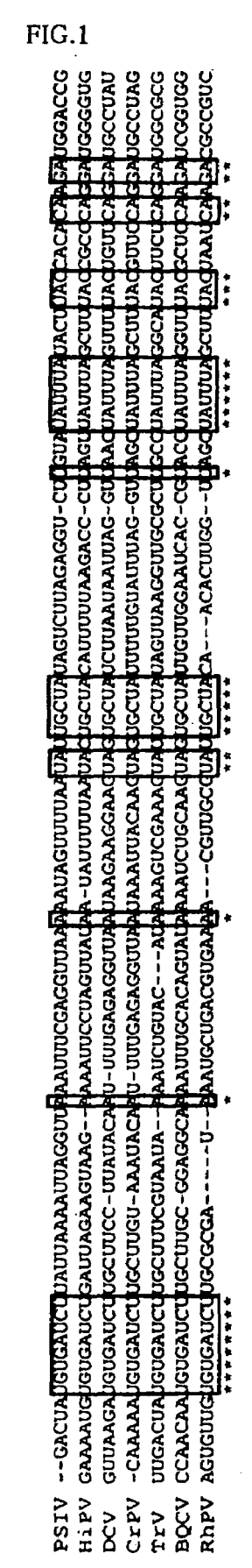
Figure 2:
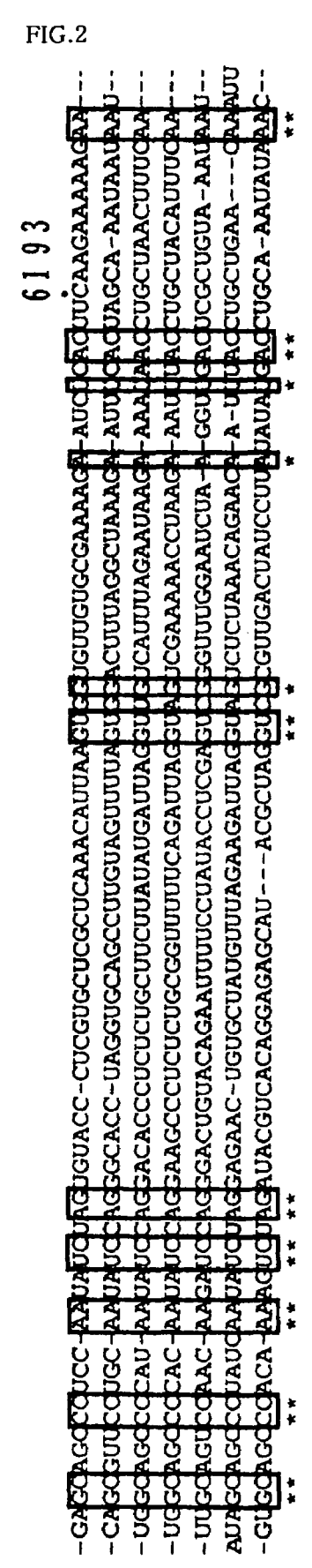

FIGS. 1 and 2 illustrate the homology of base sequences of the IGR-IRES region of CrP-like viruses. PSIV is SEQ ID NO:13; HiPV is SEQ ID NO:14; DCV is SEQ ID NO:15; CrPV is SEQ ID NO:16; TrV is SEQ ID NO:17; BQCV is SEQ ID NO:18; RhPV is SEQ ID NO: 19.

FIG. 2 is a continuation of FIG. 1. The "●" symbol in the drawing indicates the end of the IGR-IRES region and the beginning of a virus coat protein encoding region for each sequence.

BEST MODE FOR CARRYING OUT THE INVENTION

Figure 3:
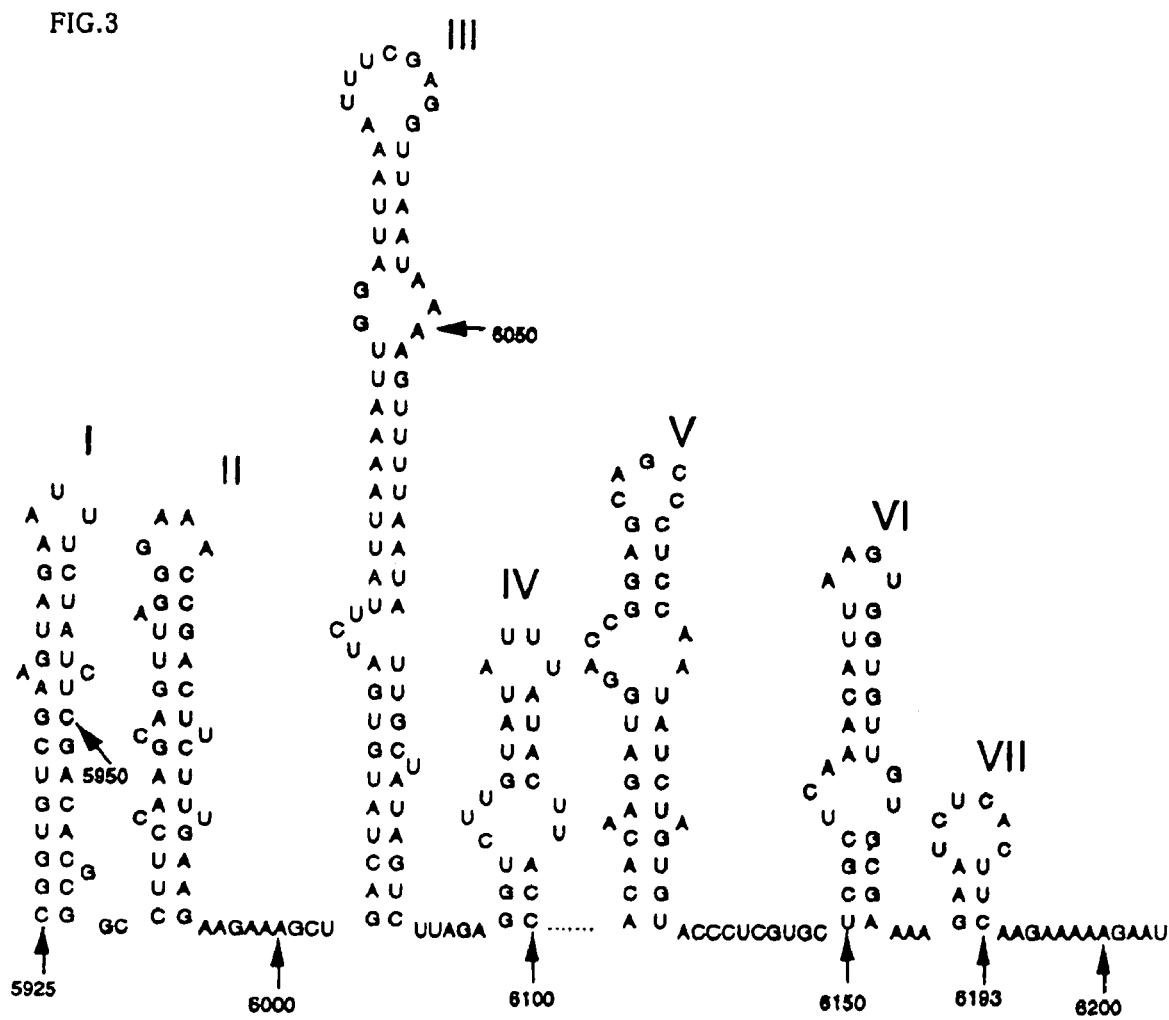
FIG. 3 illustrates a secondary structure predicted by computer program MFOLD.
Figure 4:
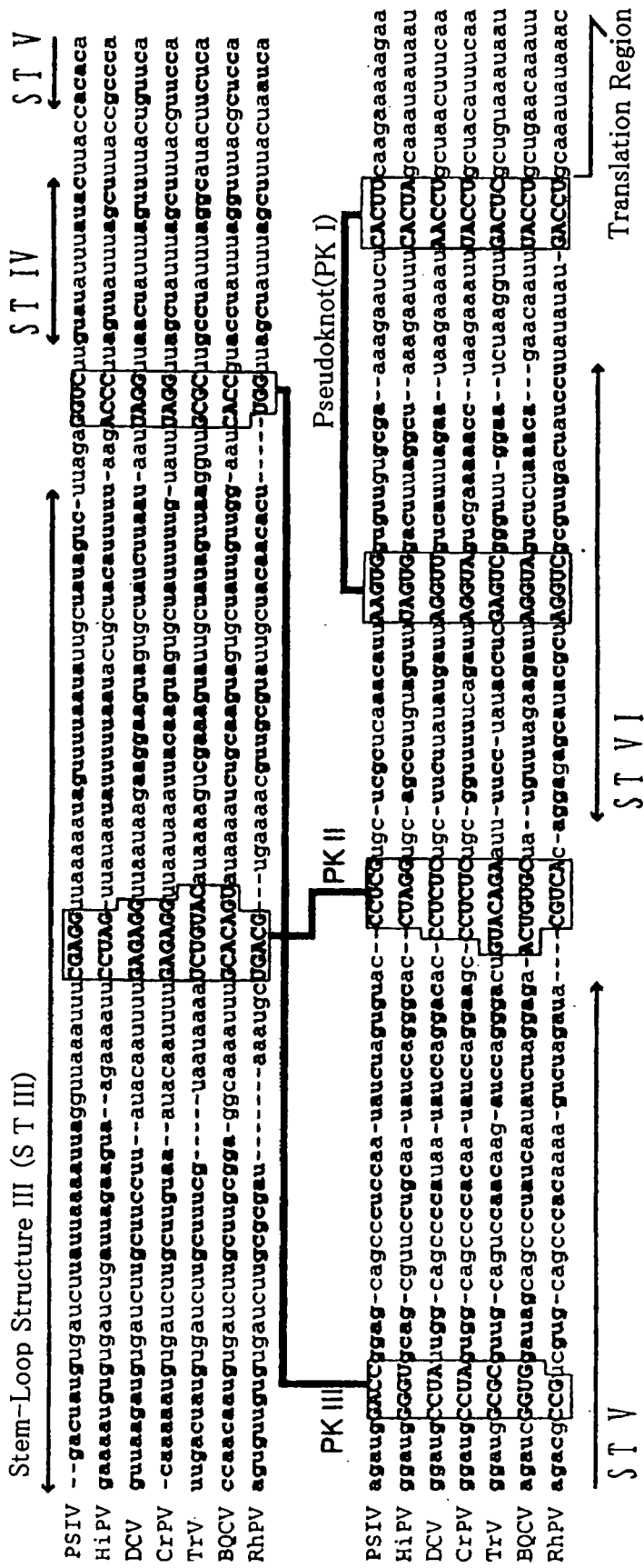
FIG. 4 shows that the higher-order structure of the IGR-IRES region of CrP-like viruses is conserved. Small bold letters indicate stem structure-forming bases, and large bold letters indicate bases involved in the base pair formation of the pseudoknot. PSIV is SEQ ID NO:13; HiPV is SEQ ID NO:14; DCV is SEQ ID NO:15; CrPV is SEQ ID NO:16; TrV is SEQ ID NO:17; BQCV is SEQ ID NO:18; RhPV is SEQ ID NO: 19. For each sequence, the IGR-IRES region ends and the virus coat protein translation region begins where indicated on the drawing.
Figure 5:
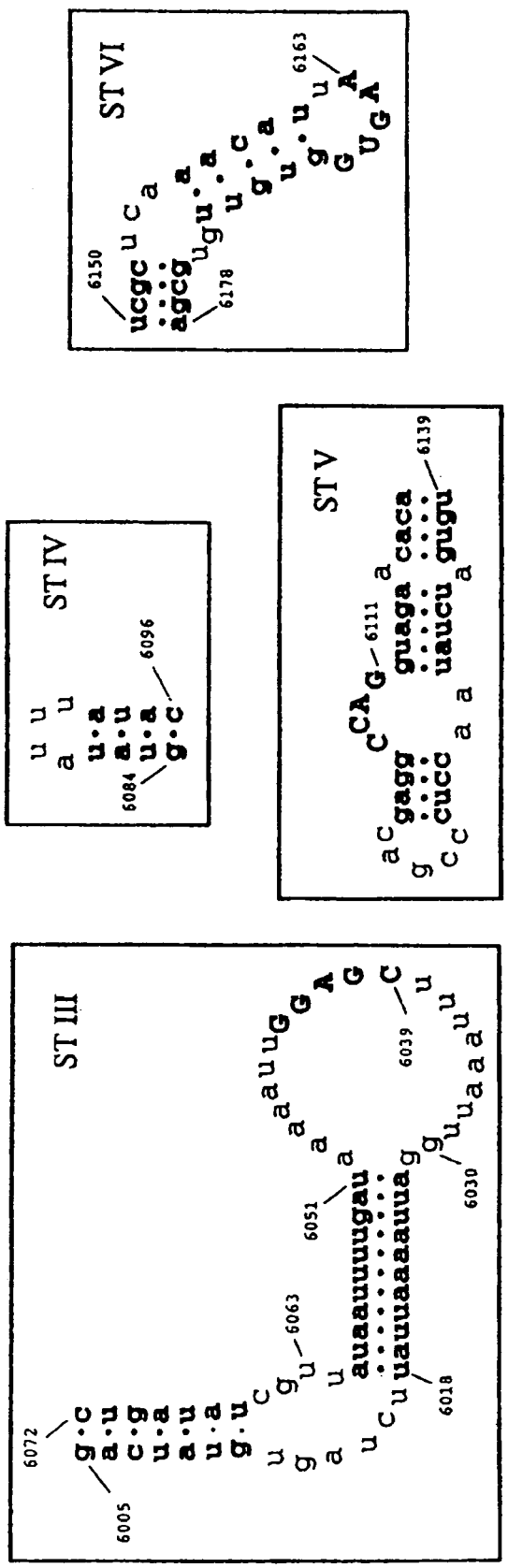
FIG. 5 illustrates a base pair of each stem structure site in PSIV. Small bold letters indicate stem structure-forming bases, and large bold letters indicate bases related to the base pair formation of the pseudoknot.
Figure 6:
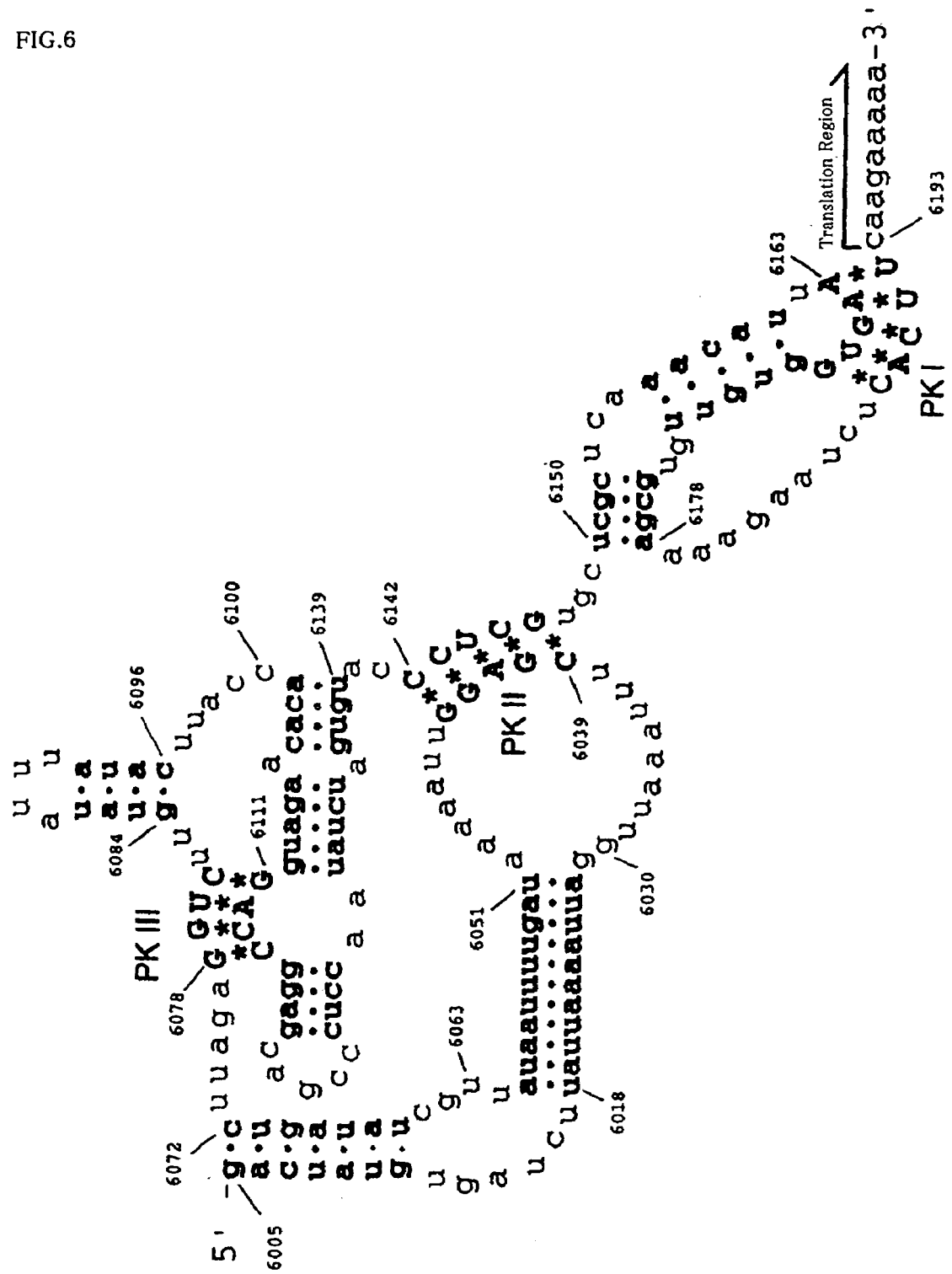
FIG. 6 illustrates the higher-order structure of IGR-IRES of PSIV based on the mutation introduction experiment. Small bold letters indicate stem structure-forming bases, and large bold letters mean bases related to the base pair formation of the pseudoknot. A numeral in these figures indicates the position of a base on the PSIV genome sequence. A dot (.) indicates a stem structure-forming base pair-forming site. An asterisk (*) indicates a base pair-forming site related to the formation of the pseudoknot structure.
Figure 7:
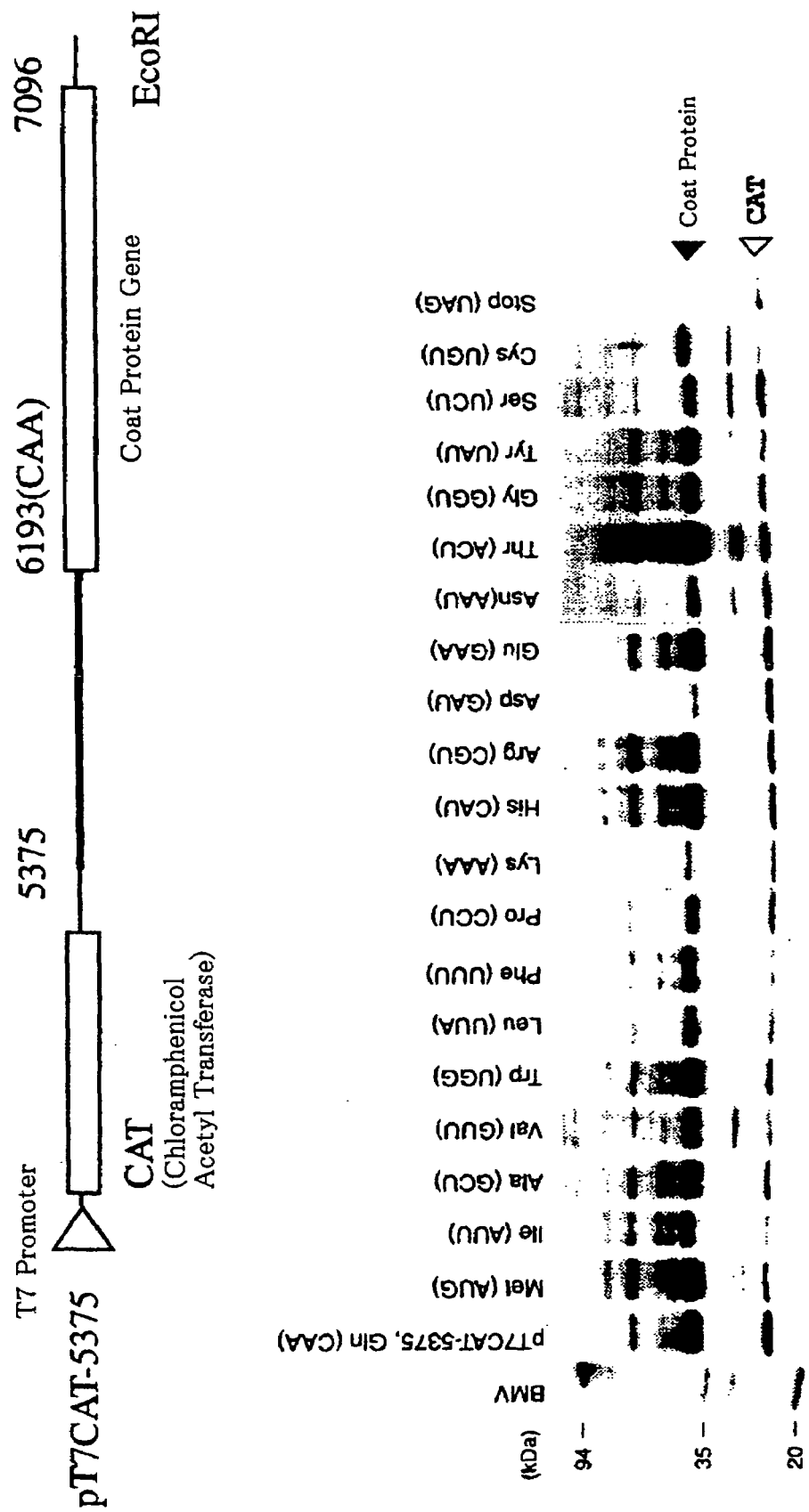
FIG. 7 illustrates, in top, the structure of plasmid pT7CAT-5375, and in bottom, an SDS electrophoresis pattern after a mutation was introduced into the first codon (CAA: glutamine) of a PSIV coat protein-coding region of pT7CAT-5375, and the translation was initiated from 20 different amino acids.

The present invention will now be described in detail. The technical and scientific terms used herein have meanings that are commonly understood by those who have ordinary knowledge in the technical field to which the present invention belongs unless otherwise defined. Various methods that are known to those skilled in the art are referred to herein. Publications or other materials disclosing such cited well-known methods are hereby incorporated by reference in its entirety. RNA higher-order structure having a function for promoting translation activity The higher-order structure of an RNA that has a function for promoting translation activity, provided by the present invention, contains a base sequence that is substantially the same as one of those shown in sequence Nos. 1–7 in the sequence list. The higher-order structure of an RNA that has the above-mentioned function for promoting translation activity consists of a base sequence constituting the RNA higher-order structure (IGR-IRES) formed upstream of the coat protein-coding region of cricket paralysis-like (CrP-like) viruses or structure homologous thereto. Even if the base sequence is not identical to one of the base sequences shown in sequence Nos. 1–7 in the sequence list, the function for promoting translation activity is kept as long as the higher-order structure similar to that of an RNA consisting of one of base sequences shown by sequence Nos. 1–7 in the sequence list is kept. In order to keep the function for promoting translation activity, it is necessary that the base sequence constituting the higher-order structure of the RNA having at least pseudoknot (PK) I, II, and III structures (knot structure based on the formation of base pairs) exists. Cricket paralysis-like viruses include PSIV (*Plautia stali* intestine virus), HiPV (himetobi P virus), DCV (Drosophila C virus), CrPV (cricket paralysis virus), TrV (*Tiatoma virus*), BQCV (black queen-cell virus), and RhPV (*Rhopalosiphum padi* virus). Base sequences of these viruses are reported in Refs. 8–15.

Base sequences substantially identical to the base sequences shown in sequence Nos. 1–7 in the sequence list are, for example, a base sequence having a homology to the base sequence shown in sequence 1 at about 50% or more, preferably at about 70% or more, more preferably at about 80% or more, and most preferably at about 95% or more. In addition, it is necessary that the base sequences substantially identical to the base sequence shown by sequence 1 in the sequence list keep at least PK (pseudoknot) I, II, and III structures or a structure homologous thereto. With respect to base sequences shown by sequences 2–7 in the sequence list also, similar examples can be shown.

The techniques for determining the homology between base sequences are well known, and a base sequence having the above-mentioned homology can be determined by widely utilizing those techniques.

In addition, based on a thus determined base sequence, a base sequence having mutation(s) including deletion, substitution, addition or insertion of one or more base(s), for example 1–30 base(s), more preferably 1–20 base(s), much more preferably 1–10 base(s), particularly preferably one to several base(s), is also provided. The means per se for introducing deletion, substitution, addition or insertion is well known. For example, the site-specific mutation-introducing method, the gene homologous recombinant method, and the polymerase chain reaction (PCR) method can be used solely or in a combination, if necessary, according to the methods described, for example, in "Molecular Cloning, a Laboratory Manual, 2nd ed., edited by Sambrook et al., Cold Spring Harbor Laboratory, 1989"; "Rabomanyuaru idenshikogaku (Labo-Manual Genetic Engineering), edited by Masami Muramatsu, Maruzen Co., Ltd., 1988"; and "PCR technology, Principle and Application of DNA Amplification, edited by Ehrich, H. E., Stockton Press, 1989" or by a method mutated by "Ulmer (Science, 219, 666, 1983)". It is necessary that any base sequence into which mutation was introduced keeps at least PK (pseudoknot) I, II, and III structures or structures homologous thereto.

In an embodiment of the present invention, the base sequence constituting the higher-order structure of the RNA having the function for promoting translation activity also indicates the strands complementary to the above-mentioned base sequences. In addition, it is necessary that those complementary strands keep at least PK (pseudoknot) I, II, and III structures or structures homologous thereto.

In another embodiment of the present invention, the base sequence constituting the higher-order structure of the RNA having the function for promoting translation activity may be a polynucleotide hybridizing to a corresponding region of the above-mentioned base sequence under a stringent condition. The condition for the hybridization can be one described, for example, in "Molecular Cloning, a Laboratory Manual 2nd ed., edited by Sambrook et al., Cold Spring Harbor Laboratory, 1989". The stringent hybridization condition is well known. For example, the following condition can be used; washing in a solution containing 50% formamide, 5×SSC (150 mM NaCl, 15 mM trisodium citrate), 50 mM sodium phosphate (pH 7.6), 5× Denhardt's solution, 10% dextransulfate, and 20 mg/ml denatured sheared salmon sperm DNA at 42° C., overnight, then washing in 0.1×SSC at about 65° C. These base sequences need not be sequences complementary to the above-mentioned base sequence if the bases hybridize to the above-mentioned base sequence as long as they keeping the objective higher-order structure. A base sequence having a homology to base sequences shown by sequences 1-7 in the sequence list or complementary sequences thereto, for example, at about 40% or more, preferably at about 70% or more, more preferably at about 80% or more, much more preferably at 90% or more, the most preferably at 95% or more can be used.

Figure 8:
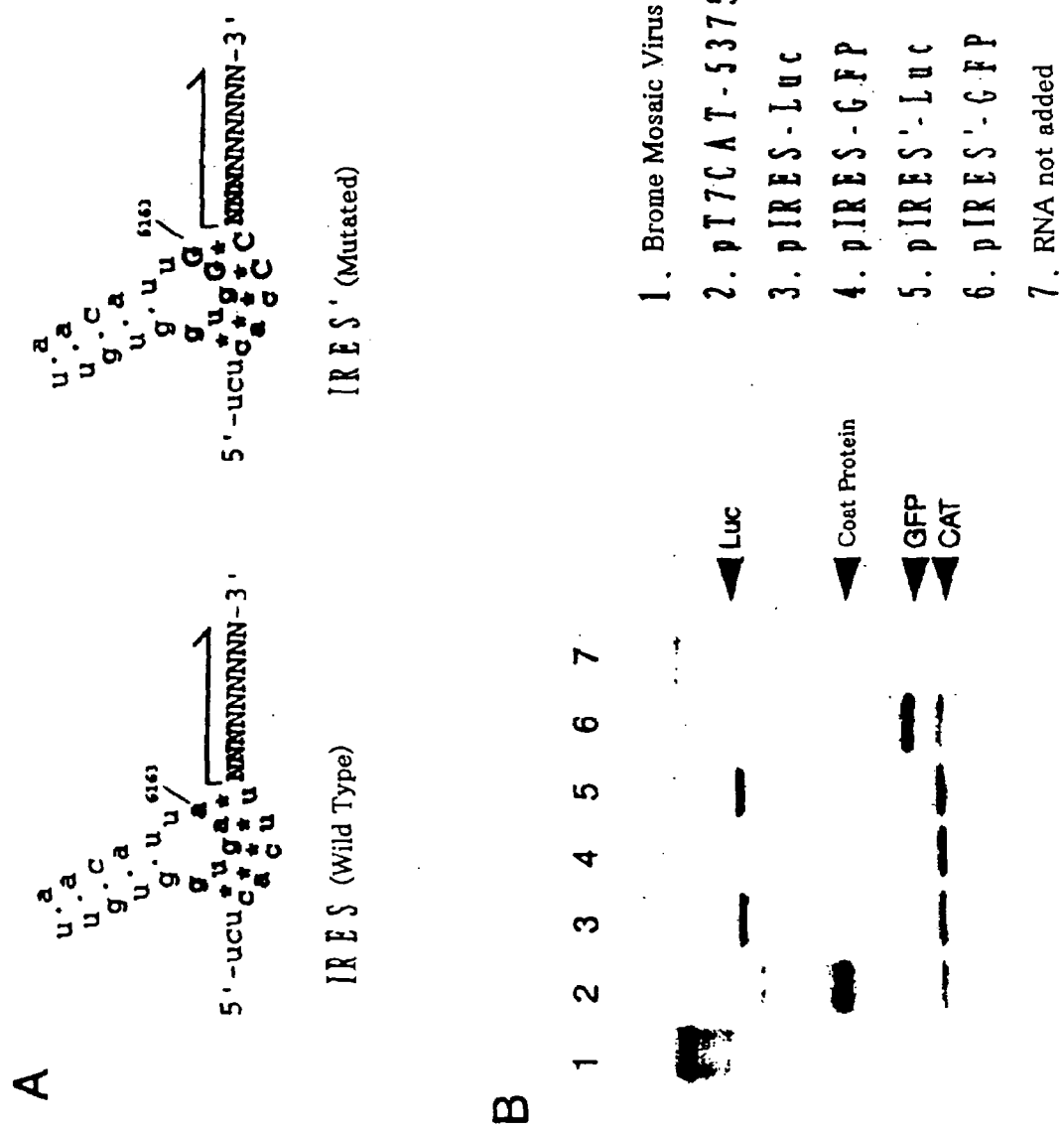
FIG. 8 illustrates the change in the combination of the base pair related to the formation of the higher-order structure immediately upstream of the translation initiation site, and the initiation of the synthesis of a protein thereby.

The higher-order structure of the above-mentioned RNA is very useful because it initiates and promotes these translations in the production not only of a homologous protein or polypeptide but also of a heterologous protein or polypeptide. "Homologous" herein means an insect virus that derives from the higher-order structure of the above-mentioned RNA, and "heterologous" means a biological species other than an insect virus. The base sequence constituting the higher-order structure of the RNA can be utilized for synthesizing a heterologous protein or polypeptide in a well-known protein-expressing system, for example, by inserting into a well known vector followed by introducing into a host cell. Also by utilizing a vector containing the base sequence constituting the higher-order structure of the RNA, a heterologous protein or polypeptide can be synthesized in a cell-free protein-expressing system (Ref. 16). As shown in the following example, although the higher-order structure of the above-mentioned RNA is a structure derived from an insect virus, translation-initiating function thereof is effective also in a house rabbit reticulocyte lysate (see FIG. 8). In addition, the function is effective not only in a translation system derived from an animal but also in a wheat germ extract that is a translation system derived from a plant (see FIG. 9).

The construction of a vector per se. is carried out utilizing a well-known means, for example, utilizing plasmid, chromosome, or virus as a replicon. Considering the stability of a gene, a more preferable system for the transformation is the integration method into the chromosome. However, it is simply carried out utilizing the autonomous replication system utilizing the extranuclear gene. The vector is selected with considering the kind of the selected host or expression system to have both a heterologous or homologous gene for expression and a gene carrying the information concerning replication and control as elements. It is preferable that the base sequence constituting the higher-order structure of the above-mentioned RNA is inserted immediate upstream of the translation region of the homologous or heterologous gene for expression. In addition, genes carrying information concerning replication and control are grouped into those derived from prokaryotic cells and those derived from eukaryotic cells, and can be utilized as a combination of promoter, ribosome-binding site, terminator, signal sequence, enhancer, marker sequence, transcription sequence, untranslated sequence, splicing, polyadenylation signal, and 5' and 3' untranslated sequences capable of stabilizing an mRNA by well-known methods.

The translated protein can be integrated into a protein expressing appropriate secretion signals to make the translated protein be excreted into an ER lumen, periplasmic base or extracellular environment. These signals can be ones intrinsic to the protein, or can be heterologous ones.

The vectors that can be used for the present invention include vectors derived from chromosome, episome and virus e.g., bacterial plasmid-derived one, bacteriophage-derived one, transposon-derived one, yeast episome-derived one, insertion element-derived one, and yeast chromosome element-derived one, vectors derived from viruses such as baculovirus, papovavirus e.g., SV40, vaccinia virus, adenovirus, fowlpox virus, pseudorabies virus and retrovirus as well as vectors obtained by combining those such as vectors derived from a genetic element of plasmid and bacteriophage, e.g., cosmid and phagemid.

Typical appropriate hosts include bacterial cells such as streptococci, staphylococci, *E. coli, Streptomyces* and *Bacillus subtilis* cells; fungi cells such as yeast cell and *Aspergillus* cell; insect cells such as *Drosophila* S2 and *Spodoptera* Sf9 cells; animal cells such as CHO, COS, HeLa, C127, 3T3, BHK, 293 and Bows melanoma cell; as well as plant cells.

The transformation by introducing a vector into a host can be carried out by methods well-known, per se. An objective heterologous protein or polypeptide can be obtained by culturing a transformant into which the vector was introduced under a well-known optimal condition for each host, followed by collecting a protein that was produced in the cultured cells or excreted into the culture broth by a well-known method.

A method for synthesizing a heterologous protein or heterologous polypeptide, which is an embodiment of the present invention, is characterized in utilizing a base sequence constituting the RNA higher-order structure as a base sequence for initiating and promoting the translation. Said method for the synthesis can be the gene recombinant technique utilizing well-known hosts such as yeast, *Bacillus subtilis*, insect cell, and animal cell, or the cell-free protein synthesis method known per se. Although the protein synthesis was confirmed utilizing the cell-free protein synthesis method using a house rabbit reticulocyte lysate or wheat embryo extract as a ribosome source in the examples of the present invention, it is not limited thereto.

In the conventional genetic engineering technique, the AUG translation initiation codon coding methionine was needed when a protein was synthesized, and the obtained protein has methionine at the amino end. By using the higher-order structure of the above-mentioned RNA, however, the translation can be initiated even if the translation first codon is a base sequence coding any amino acid without using AUG translation initiation codon. Namely, utilizing the higher-order structure of the above-mentioned RNA permits synthesizing a protein having an arbitrary amino acid at the amino terminus.

In addition, changing one or more of combinations of base pairs constituting PK, particularly base pairs that constitute PKI and locate immediately upstream of the translation initiation site among the higher-order structures of the above-mentioned RNA permits initiating the synthesis of an arbitrary protein from an arbitrary codon. When the number of the combination of the base pairs to be changed is two or more, the combination of the base pairs can be a continuous combination, or can be a discontinuous combination. When the higher-order structure locating immediately upstream in the translation initiation site of PKI of PSIV was mutated, for example, from cacuu to caccc, a heterologous protein GFP was translated that was not translated by the plasmid before modification. Namely, changing the combination of base pairs constituting PK, particularly the combination of base pairs that constitute PKI and locate immediately upstream in the translation initiation site, might permits translating a protein from a heterologous gene that cannot be translated by a wild-type IGR-IRES. The higher-order structure of RNA in which the above-mentioned combination of base pairs was changed should keep at least PK (pseudoknot) I, II, and III structures or structure homologous thereto.

EXAMPLES

The present invention will specifically be described based on examples, but the present invention is not limited to the examples below.

Example 1

The base sequences of the IGR-IRES region of CrP-like viruses (Ref. 8) were aligned using a computer program CLUSTAL W to give a homology on the primary structure as shown in FIGS. 1 and 2. The region surrounded by black lines in FIGS. 1 and 2 indicates a conserved sequence. Even this method, however, could not detect any conservation concerning the complementary sequence playing an important role in the function of IRES. The result of the prediction of the IGR-IRES region of PSIV that is a member of CrP-like viruses with a secondary structure-predicting program MFOLD is shown in FIG. 3. This method did not permit detecting any conservation concerning the complementary sequence playing an important role in the function of IRES, either. Therefore, in order to obtain the information concerning common properties of the IGR-IRES region and the functionally important structure of CrP-like viruses, a mutation introduction experiment was carried out by a method described below. First, bases in the stem-loop structure and pseudoknot structure (knot structure based on base pair formation) were mutated, and the effect of the mutation to the protein synthesis was examined to investigate the higher-order structure. As a result, showing in FIGS. 4–6, aligning the base sequences that are important for the function of IGR-IRES and extracted permitted showing that the higher-order structure shown by FIGS. 5 and 6 can be formed with respect to all the CrP-like viruses. The formation of four stem-loop structures (ST III, ST IV, ST V, and ST VI) and three pseudoknot structures (PK I, PK II, and PK III) was confirmed for each virus. Deletion of the three pseudoknot structures among said higher-order structures did not permit translation. In addition, it was found that the base sequence locating downstream in the translation initiation site was not related to the higher-order structure of IGR-IRES. This suggests that the reason why translation was inhibited when a different gene was introduced downstream in previous reports (Refs. 1 and 6) is that such a sequence was inserted that the formation of the higher-order structure of IGR-IRES was inhibited. The above-mentioned results showed that the higher-order structure containing three pseudoknot structures contributes to the initiation and acceleration of translation of a protein.

Experimental Example 1

Translating a protein by linking a reading frame of a gene downstream in the higher-order structure permited initiating the translation of the protein from various amino acids. (FIG. 7). Namely, even if the first translation codon was changed, the synthesis of the protein could be initiated. Even if any codon corresponding to each of all twenty amino acids was the first translation codon, the protein was synthesized.

Then, using the same plasmid as used for the above-mentioned mutation introduction experiment, in place of the virus coat protein gene, after deleting the AUG translation initiation codon, luciferase gene and jelly fish green fluorescent protein (GFP) gene were inserted immediately downstream of PKIII, and were made be expressed by the method described below (FIG. 8). Although the luciferase gene was translated from downstream of wild-type IGR-IRES, the GFP gene was not translated. To improve the above, the base sequence of PKI that is a part of the sequence of IGR-IRES, was mutated from wild-type cacuu (FIG. 8A, left) to caccc (FIG. 8A, right). Said modification permitted translating the GFP gene. Thus, changing the combination of base pairs involved in the formation of the higher-order structure locating immediately upstream in the translation initiation site permitted establishing a method for initiating the synthesis of an arbitrary protein from an arbitrary codon (FIG. 8). With respect to lane 1 of FIG. 8B, BMV indicates brome mosaic virus RNA. With respect to lane 2, pT7CAT-5375 indicates a plasmid whose expression protein is a coat protein and whose initiation codon is CAA (Gln). With respect to lane 3, pIRES-Luc indicates a plasmid in which PKI is the wild type, and an expression protein is luciferase, and aug is lacking. With respect to lane 4, PIRES-GFP indicates the case in which GFP was used as an expression protein in lane 3. With respect to lane 5, pIRES'-Luc indicates the case in which a plasmid in which PKI is a mutant, and an expression protein is luciferase, and aug is lacking. With respect to lane 6, pIRES'-GFP indicates the case in which GFP was used as an expression protein in lane 5. With respect to lane 7, RNA was not added, i.e., the control. Luc stands for luciferase. CAT stands for chloramphenicol acetyl transferase. GFP stands for green fluorescent protein.

Experiments Were Carried Out as Follows

Construction of Mutant Plasmid

Plasmid pT7CAT-5375 was used as a vector. The pT7CAT-5375 was a vector prepared by inserting chloramphenicol acetyl transferase (CAT) gene downstream of the promoter sequence recognized by T7RNA polymerase derived from a phage of *Escherichia coli*, as described in Ref. 1, followed by linking each base sequence (translation acceleration sequence) having the higher-order structure according to the present invention and a gene coding an appropriate protein further downstream thereof (see Japan Patent No. 3002724). PSIV coat protein gene was used as the gene coding the protein in the experimental example. An RNA was synthesized from the plasmid with T7RNA polymerase, and in vitro translation was carried out in a house rabbit reticulocyte using the RNA. Obtained translation products were separated by the SDS-polyacrylamide electrophoresis.

The amplification of the mutant fragments was carried out using synthesized DNA primers containing mutation sequences and a high fidelity DNA polymerase (KOD Dash, Toyobo Co., Japan), and the amplified fragments were purified by the agarose electrophoresis, phosphorylated, self-ligated, and transformed in *Eseherichia coli*. Substitution of the nucleotide was confirmed by DNA-sequencing. Deletion and substitution of the spiral part of stem loop III was carried out by the fusion PCR (Virology 214, 611–618 (1995)). A forward primer (GGTTAAATTTCAGG-TAAAAAATTGCTATA), SEQ ID NO. 8, containing nt6029-6050 and nt6062-6080 of PSIV sequence and a reverse primer containing nt27-5 of pT7Blue (Novagen, Inc.) were synthesized for the initial amplification to delete nucleotide (nt) 6051-6061. Then, a reverse primer (CCTC-GAAATTTAACCAGATCACATAGTCAGCTTTC), SEQ. ID. NO. 9, containing nt6043-6029 and nt6017-5998 of PSIV sequence and a forward primer containing nt28-47 of pT7Blue (Novagen, Inc.) were synthesized for another initial amplification to delete nt6028-60 18. Underlines of these primers indicate 15 nt overlap of the fusion PCR. After each initial amplification using these two primer sets, two amplified DNA fragments were mixed and fused according to the description in Ref. 17. The final amplification was carried out using primers carrying nt28-47 and nt27-5 of pT7Blue, and the amplified DNA fragments were purified with a gel, phosphorylated, and ligated. The initial amplification was carried out using longer primers containing a substituted nucleotide to substitute the helical part.

In Vitro Translation Analysis by Mutant PSIV-IRES

Plasmid DNA was linearized at nt7096 of the coat protein-coding region of PSIV genome with a restriction enzyme EcoRI derived from *Escherichia coli*. The linearized DNA was transcribed with T7RNA polymerase using Ribo-MAX large-scale RNA production system (Promega Corp.). Biotin in vitro Translation Kit (Roche Diagnostics Corp.) was used to label the translation products. RNA dissolved in distilled water was heated at 68° C., chilled on ice, and mixed with a house rabbit reticulocyte lysate. When the compensatory mutation analysis was carried out, the final concentration of RNA was adjusted to 4 µg/ml. When deletion was analyzed, the concentration of RNA was enhanced to 16 µg/ml to detect a small amount of the coat protein. Biotinylated proteins were isolated by the SDS-polyacrylamide (12%) gel electrophoresis, transferred onto a PVDF membrane, and detected using ECL Western Blotting Reagents (Amersham Pharmacia Biotech Ltd.).

Experimental Example 2

Figure 9:
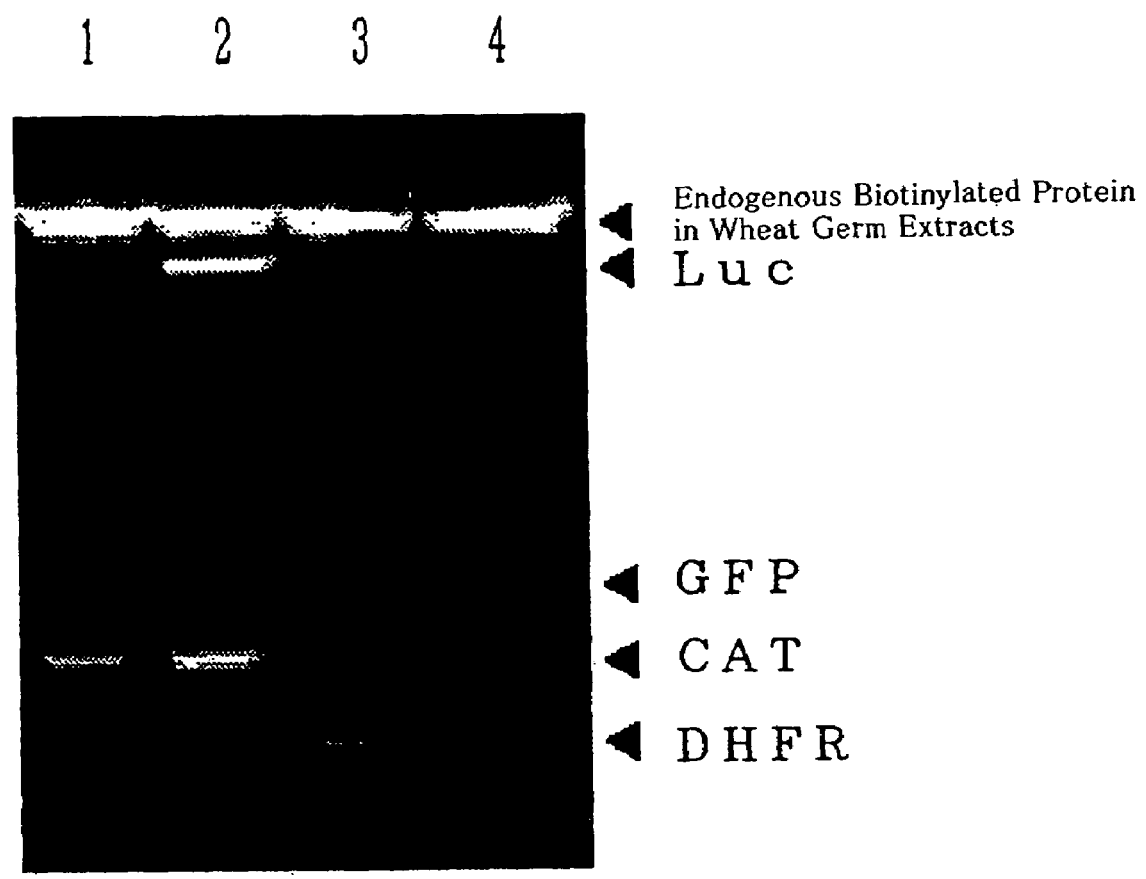
FIG. 9 illustrates an electrophoresis pattern showing that a heterologous protein is expressed by the PSIV-IRES higher-order structure in a cell-free protein synthesis system using a wheat germ extract.

The cell-free protein synthesis was carried out according to the method described in Refs. 18 and 19 using a commercially available wheat germ extract (Promega Corp.) as a source of ribosome. The same plasmid used in the Example 1 was used. Luciferase gene or jelly fish GFP gene was inserted immediately downstream of PK I of the plasmid in a manner similar to the Example 1 after deleting the aug initiation codon in place of the virus coat protein gene. In addition, a dihydrofolate reductase (DHFR) gene derived from *Eschenichia coli* was inserted immediately downstream in the site where mutated PSIV-IRES was inserted immediately downstream T7 promoter sequence of the plasmid, after the AUG codon was deleted. IRES was used that was mutated by mutating nt6006-6007 from ac to gg, nt6070-6071 from gu to cc, and nt6165 from g to c, and nt6190 from c to g. A template RNA was made to be expressed, in a manner similar to the Example 1, from a plasmid constructed with respect to each gene. Each of these template RNAs (final concentration=0.25 mg/mL) and 10 pmol of biotinylated lysyl tRNA (Roche Diagnostics Corp.) were added to a commercially available wheat germ extract reaction mixture (25 µL), and subjected to the translation reaction at 23° C. for 2 h. Reagents and conditions for the cell-free protein translation reaction using the wheat germ extract were according to the description disclosed in Refs.18 and 19. Then, the translation products were detected by the method similar to that of the Example 1. The results are illustrated in FIG. 9, in which lane 1 is a result of the protein synthesis using pIRES'-GFP that is the same RNA as used in lane 6 of FIG. 8, and lane 2 is a result of the protein synthesis using pIRES'-Luc that is the same RNA as used in lane 5 of FIG. 8, and lane 3 is a result of the use of the AUG codon-deleted DHFR gene prepared in an above-described manner, and lane 4 is the control to which RNA was not added. As is apparent from FIG. 9, utilizing the mutated PSIV-IRES permitted translating a heterologous protein gene that does not begins with the AUG codon, i.e., synthesizing a heterologous protein or polypeptide that begins with an arbitrary amino acid in a cell-free protein synthesis system not only using a house rabbit reticulocyte lysate but also using a wheat germ extract.

References

Ref. 1: Sasaki J & Nakashima N. J Virol. 73, 1219–1226 (1999)
Ref. 2: Sasaki J & Nakashima N. Proc. Natl. Acad. Sci. USA. 97, 1512–1515(2000)
Ref. 3: RajBhandary Proc. Natl. Acad. Sci. USA. 97, 1325–1327(2000)
Ref. 4: Willson et al. Mol. Cell. Biol. 20, 4990–4999(2000)
Ref. 5: Wilson et al. Cell, 102, 511–520(2000)
Ref. 6: Domier et al. Virology, 268, 264–271(2000)
Ref. 7: McCarthy J E G Cur. Biol. R715–717(2000)
Ref. 8: van Regenmortel VIRUS TAXONOMY. Seventh report of the international committee on taxonomy of viruses. Academic Press, San Diego pp 1162–683(2000)
Ref. 9: Sasaki J. et al. Virology 244, 50–58(1998).
Ref. 10: Nakashima N. et al. Arch. Virol. 144, 2051–2058 (1999)
Ref. 11: Johnson K N & Christian P D J. Gen. Virol. 79, 191–203(1998)
Ref. 12: Wilson J E. et al. Mol. Cell. Biol. 20, 4990–4999 (2000)
Ref. 13: Czibener C. et al. J. Gen. Virol. 81, 1149–1154 (2000)
Ref. 14: Leat N et al. J. Gen. Virol. 81, 2111–2119(2000)
Ref. 15: Moon J S. et al. Virology 243, 54–65(1998)
Ref. 16: Nature 179, 160–161 (1957)
Ref. 17: Virology 214, 611–618 (1995)
Ref. 18: Endo Y. et al. J Biotech 25, 221–230(1992)
Ref. 19: Madin K. et al. Proc. Natl. Acad. Sci. USA 97, 559–564(2000)

Industrial Applicability

As set forth hereinabove, the present invention provides a base sequence constituting a specific higher-order structure having a translation acceleration function, and a method that permits synthesizing a heterologous protein or polypeptide without being restrained by the initiation codon (without containing AUG initiation codon) using the base sequence. The present invention provides a great usefulness in the synthesis technique utilizing the gene recombinant technique for a heterologous protein or polypeptide, and will make a great contribution to a wide field ranging from the basic research such as synthesis and structure analysis of protein to the development and production of medicines as its application.

What is claimed is:

1. A method for synthesizing a heterologous protein or a heterologous polypeptide comprising the steps of
providing a cell-free protein expressing system,
providing a polynucleotide encoding the heterologous protein or heterologous polypeptide and a polynucleotide that promotes translation activity, wherein the polynucleotide that promotes translation activity has an RNA higher-order structure including PK (pseudoknot) I, II, and III structures and is selected from:
1) one of the base sequences of SEQ ID NOs: 1–7;
2) a base sequence of SEQ ID NO: 1, except that positions 187–188 of the base sequence of SEQ ID NO: 1 are cc instead of uu and positions 159–160 are gg instead of aa; and
3) a base sequence containing the base sequence of 1) or 2); and
wherein the polynucleotide encoding the heterologous protein or heterologous polyptptide is immediately downstream from the PKI structure of the polynucleotide that promotes translation activity,
translating the polynucleotide encoding the heterologous protein or heterologous polypeptide in the cell-free protein expressing system to form the heterologous protein or heterologous polypeptide, wherein the translating is initiated and/or promoted by the polynucleotide that promotes translation activity, and
isolating the heterologous protein or heterologous polypeptide.

2. The method for synthesizing a heterologous protein or a heterologous polypeptide according to claim 1, wherein the synthesis is carried out without using AUG translation initiation codon.

3. The method for synthesizing a heterologous protein or heterologous polypeptide according to claim 1, wherein the RNA higher-order structure comprises a base sequence selected from one of the sequences of SEQ ID NOs:1–7.

4. The method for synthesizing a beterologous protein or a heterologous polypeptide according to claim 3 wherein the synthesis is carried out without using AUG translation initiation codon.

5. The method for synthesizing a heterologous protein or heterologous polypepfide according to claim 1, wherein the RNA higher-order structure comprises the base sequence of SEQ ID NO:1.

6. The method for synthesizing a heterologous protein or heterologous polypeptide according to claim 1, wherein the RNA higher-order structure comprises the base sequence of SEQ ID NO:1, except that positions 187–188 of the base sequence of SEQ ID NO:1 are cc instead of uu and positions 159–160 are gg instead of aa.

7. The method for synthesizing a heterologous protein or heterologous polypeptide according to claim 1 wherein the protein expressing system is a wheat germ extract.

8. The method for synthesizing a heterologous protein or a heterologous polypeptide according to claim 7, wherein the synthesis is carried out without using AUG translation initiation codon.

9. A method for initiating synthesis of an arbitrary heterologous protein or heterologous polypeptide from an arbitrary codon which comprises the steps of
providing a cell-free protein expressing system,
providing a polynucleotide encoding the arbitrary heterologous protein or heterologous polypeptide and a polynucleotide that promotes translation activity, wherein the polynucleotide that promotes translation activity has PK (pseudoknot) I, II, and III structures in a RNA higher-order structure having a function for promoting a translation activity, wherein the polynucleotide encoding the heterologous protein or heterologous polyptptide is immediately downstream from the PKI structure of the polynucleotide that promotes translation activity and wherein the RNA higher-order structure has a base sequence selected from:

1) one of the base sequences of SEQ ID NOs: 1–7;
2) abase sequence of SEQ ID NO: 1, except that positions 187–188 of the base sequence of SEQ ID NO: 1 are cc instead of uu and positions 159–160 are gg instead of aa; and
3) a base sequence containing the base sequence of 1) or 2), translating the polynucleotide encoding the arbitrary heterologous protein or heterologous polypeptide from an arbitrary codon in the cell-free protein expressing system to form the heterologous protein or heterologous polypeptide, wherein the translating is initiated and/or promoted by the polynucleotide that promotes translation activity, and isolating the heterologous protein or heterologous polypeptide.

10. The method for initiating the synthesis according to claim 9, wherein the RNA higher-order structure comprises the base sequence of SEQ ID NO:1, except that positions 187–188 of the base sequence of SEQ ID NO:1 are cc instead of un and positions 159–160 are gg instead of aa.

* * * * *

UNITED STATES PATENT AND TRADEMARK OFFICE
CERTIFICATE OF CORRECTION

PATENT NO. : 7,138,515 B2  Page 1 of 1
APPLICATION NO. : 10/088750
DATED : November 21, 2006
INVENTOR(S) : Nakashima et al.

It is certified that error appears in the above-identified patent and that said Letters Patent is hereby corrected as shown below:

IN THE CLAIMS:

Claim 1, column 15, line 49, "polyptptide" should read --polypeptide--.

Claim 9, column 16, line 64, "polyptptide" should read --polypeptide--.

Signed and Sealed this

Twenty-second Day of May, 2007

JON W. DUDAS
*Director of the United States Patent and Trademark Office*